US012685506B2

(12) United States Patent
Gerlach et al.

(10) Patent No.: US 12,685,506 B2
(45) Date of Patent: Jul. 21, 2026

(54) ALIGNMENT OF IMAGES FROM A MULTI-MODALITY IMAGING SYSTEM

(71) Applicant: Siemens Medical Solutions USA, Inc., Malvern, PA (US)

(72) Inventors: Keith Gerlach, Knoxville, TN (US); Shikui Yan, Knoxville, TN (US); Paul Schleyer, Knoxville, TN (US); Riley Toll, Knoxville, TN (US); Mariah Crosby, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 150 days.

(21) Appl. No.: 18/830,656

(22) Filed: Sep. 11, 2024

(65) Prior Publication Data

US 2025/0248679 A1     Aug. 7, 2025

Related U.S. Application Data

(60) Provisional application No. 63/550,730, filed on Feb. 7, 2024.

(51) Int. Cl.
    *A61B 6/58*      (2024.01)
    *A61B 6/03*      (2006.01)

(52) U.S. Cl.
    CPC .............. *A61B 6/584* (2013.01); *A61B 6/032* (2013.01); *A61B 6/037* (2013.01)

(58) Field of Classification Search
    CPC ......... A61B 6/584; A61B 6/032; A61B 6/037; A61B 6/4417
    See application file for complete search history.

(56) References Cited

U.S. PATENT DOCUMENTS

| | | | |
|---|---|---|---|
| 7,569,829 B2 | 8/2009 | Chen et al. | |
| 8,077,943 B2 | 12/2011 | Williams et al. | |
| 2003/0073895 A1* | 4/2003 | Nields .................. | A61B 6/5247 600/407 |

OTHER PUBLICATIONS

Fisher et al., "Camera-based Motion Correction for PET/MR Brain Imaging," 2022 IEEE Nuclear Science Symposium and Medical Imaging conference, 3 pages. (Year: 2022).*

* cited by examiner

*Primary Examiner* — Kiho Kim

(57) ABSTRACT

A framework for aligning images from a multi-modality imaging system. A first image of a phantom positioned on a patient table may be acquired using a first camera of first modality in the multi-modality imaging system. The phantom may include first and second hot rods, as well as first, second and third cold rods. The first and second hot rods are disposed in a plane that is substantially orthogonal to a travel vector of the patient table, while the first and second cold rods are substantially orthogonal to the travel vector, and the third cold rod is substantially parallel to the travel vector. A second image of the phantom may be acquired using a second camera of second modality in the multi-modality imaging system. Misalignment parameters of the first and second cameras may be determined based on the first and second images.

20 Claims, 11 Drawing Sheets

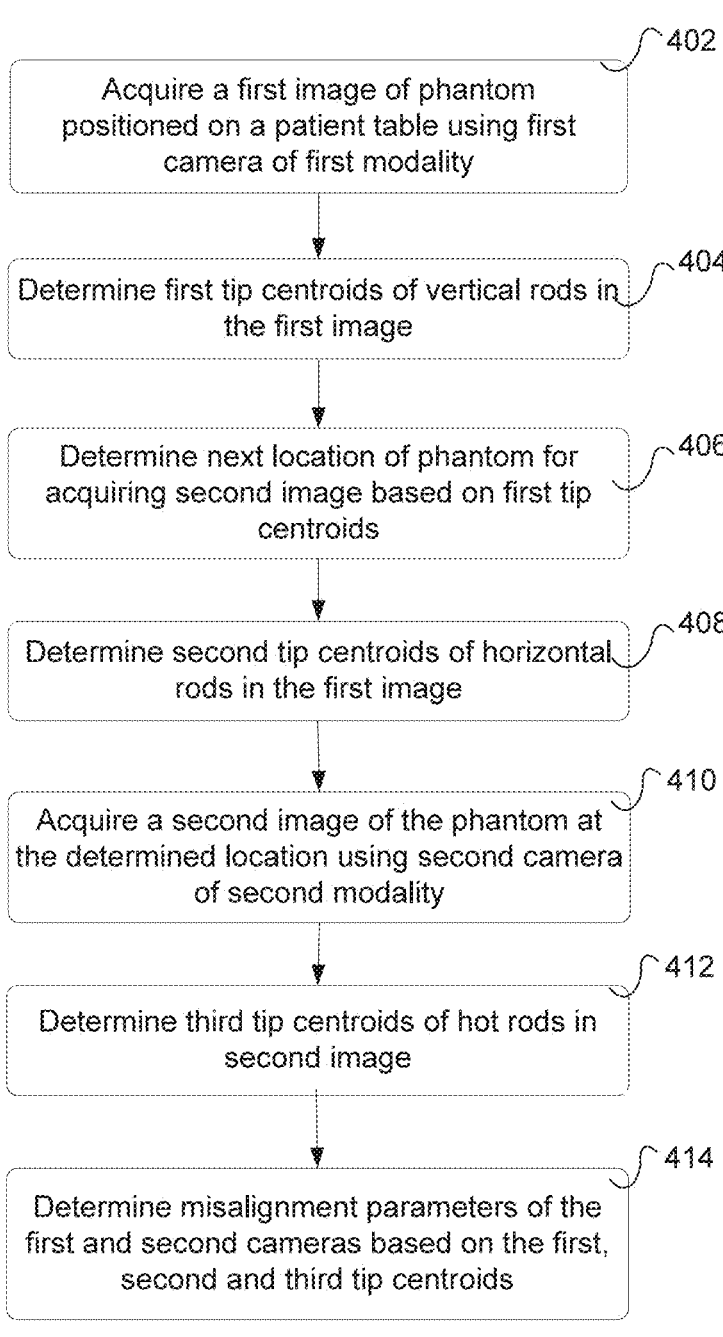

402

Acquire a first image of phantom positioned on a patient table using first camera of first modality

404

Determine first tip centroids of vertical rods in the first image

406

Determine next location of phantom for acquiring second image based on first tip centroids

408

Determine second tip centroids of horizontal rods in the first image

410

Acquire a second image of the phantom at the determined location using second camera of second modality

412

Determine third tip centroids of hot rods in second image

414

Determine misalignment parameters of the first and second cameras based on the first, second and third tip centroids

| Parameter Space | Misalignment Parameters | New gantry offset fixture | | |
|---|---|---|---|---|
| | | From cold rods | From hot rods | From both |
| Relative translation & rotation (PET to CT) | X | | ✓ | |
| | Y | | ✓ | |
| | Z | | ✓ | |
| | Pitch | | ✓ | |
| | Yaw | | ✓ | |
| | Roll | | ✓ | |
| Absolute Pitch/Yaw (CT to PHS) | Pitch | ✓ | | |
| | Yaw | ✓ | | |
| Absolute Pitch/Yaw (PET to PHS) | Pitch | | | ✓ |
| | Yaw | | | ✓ |

*Fig. 6*

ALIGNMENT OF IMAGES FROM A MULTI-MODALITY IMAGING SYSTEM

CROSS-REFERENCE TO RELATED APPLICATION

The present application claims the benefit of U.S. provisional application No. 63/550,730, filed Feb. 7, 2024, the entire contents of which are herein incorporated by reference.

TECHNICAL FIELD

The present disclosure generally relates to medical imaging, and more particularly to alignment of images from a multi-modality imaging system.

BACKGROUND

In the field of medical image technology, Positron Emission Tomography (PET) or gamma cameras are often combined with Computed Tomography (CT) systems. A PET/CT imaging system typically includes a CT camera with a tunnel for the patient, a PET camera with a tunnel for the patient, and a patient handling system (PHS) including a patient table to move the patient axially through each camera. Both PET and CT cameras are rigidly mounted, and are nominally orthogonal to the table travel vector, and nominally concentric about an axis parallel to the table travel.

However, in any actual installation, neither camera is perfectly orthogonal to the table travel vector. Additionally, the two cameras are usually not perfectly concentric, and the axial distance between the two cameras is not as perfect as designed. Due to the gantry offset, a quality check needs to be performed for proper alignment of three-dimensional (3D) images from each camera.

SUMMARY

Described herein is a framework for alignment of images from a multi-modality imaging system. A first image of a phantom positioned on a patient table may be acquired using a first camera of first modality in the multi-modality imaging system. The phantom may include first and second hot rods, as well as first, second and third cold rods. The first and second hot rods are disposed in a plane that is substantially orthogonal to a travel vector of the patient table, while the first and second cold rods are substantially orthogonal to the travel vector, and the third cold rod is substantially parallel to the travel vector. A second image of the phantom may be acquired using a second camera of second modality in the multi-modality imaging system. Misalignment parameters of the first and second cameras may be determined based on the first and second images.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

FIG. 4 shows an exemplary method of image alignment;

FIG. 6 shows a table of exemplary misalignment parameters that may be determined for a CT-PET imaging system using the present framework;

DETAILED DESCRIPTION

Figure 1:
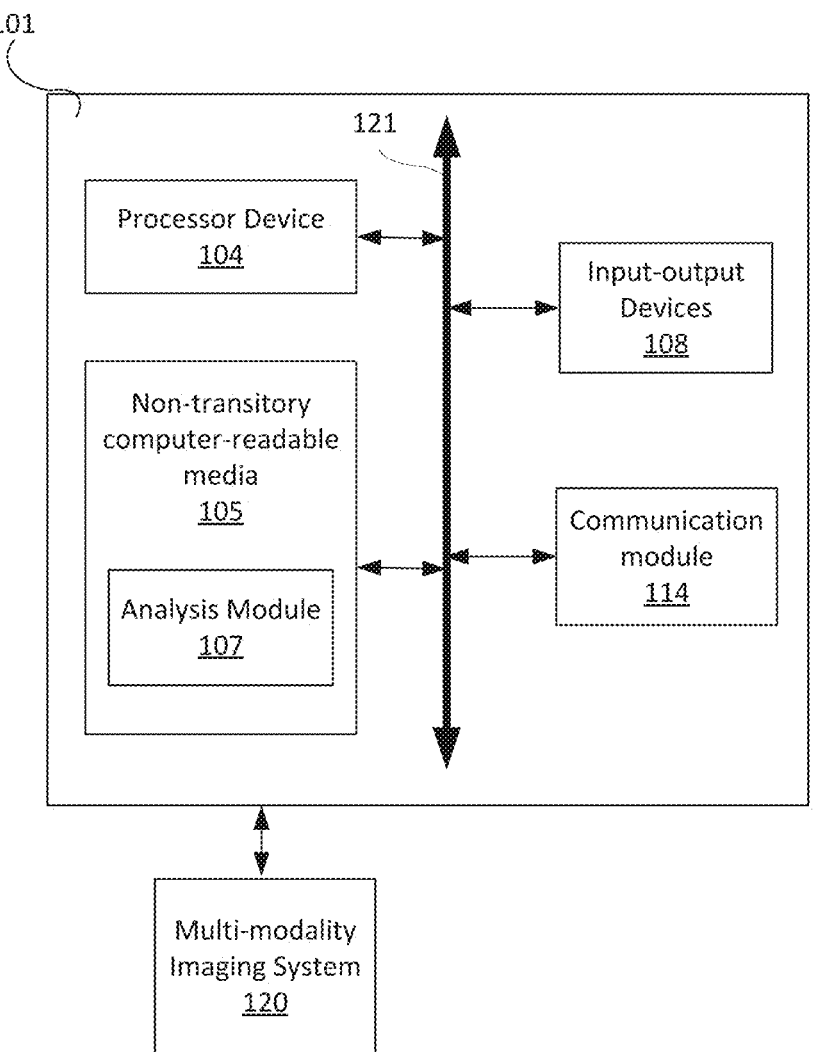
FIG. 1 is a block diagram illustrating an exemplary computer system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

Measurement of the angles of each camera in a multi-modality imaging system and the translational offsets between the cameras is needed for quality control of the installation and for proper alignment of three-dimensional (3D) images from each camera. This measurement requires imaging a device or phantom which includes material that can be seen by both cameras, such that the location of this material may be correlated between the two image volumes acquired by the two cameras. Cameras of different modalities detect different types of materials. For example, a CT camera detects dense material, while a PET camera detects only certain types of radioactive material.

Traditional systems are not capable of detecting angles (e.g., pitch and yaw) of the CT camera with respect to the table travel, nor the angles of the CT camera with respect to the PET camera. Known devices utilize Na-22 point sources, while the present framework utilizes Ge-68 sources, which avoids requiring the customer to obtain a site license to handle an additional isotope, and avoids the exposure of users to the direct gamma photons produced by Na-22.

The present framework utilizes an imaging phantom that has at least two hot features and at least three cold features of known geometry. A hot feature generally refers to a material that can be seen in images with the same centroid acquired by both cameras (e.g., CT and PET) in a multi-modality imaging system. A cold feature generally refers to a material that can be seen only in the image acquired by one camera (e.g., CT) but not the image acquired by the other camera (e.g., PET) in a multi-modality imaging system. In some implementations, the two hot features are rods oriented nominally vertically and nominally left-right horizontally respectively in the phantom, such that they can be used to measure the relative pitch and yaw angles between the two cameras. The hot features are used to provide the relative camera offsets in the translational and roll angle (about the travel vector) directions. The cold features may include, for example, one nominally vertical rod, one nominally left-right horizontal rod, and one nominally axial horizontal rod, all substantially orthogonal to each other within a tolerance that maintains intended functional performance. The cold features may be used to measure the camera pitch and yaw angles with respect to the table travel vector.

Advantageously, this framework does not depend upon accurate orientation of the phantom with respect to the cameras. Orientation within approximately 10 degrees of orthogonal with respect to the cameras and the table travel vector may be sufficient. The phantom may further include orientation marks, which can be aligned with light or laser markers to ensure adequate alignment.

A previous device incorporated two hot line features, both at relatively small angles with respect to the travel of the device through the CT camera. In this orientation, and for the acquisition method which includes moving the device axially through the relatively narrow CT camera field of view, the angles of the lines in the CT image were very insensitive to pitch or yaw angles of the CT camera. After acquisition of the PET image, acquired with the device not moving, the resulting calculation of offsets between the two images was only able to measure the pitch and yaw angles of the PET camera with respect to the table travel vector, but contained no information about the pitch and yaw angles of the CT camera.

With the addition of three substantially orthogonal cold line features and reorientation of the two hot lines in the phantom, the present framework can measure all angles (i.e., pitch and yaw angles) of both cameras in addition to relative offsets between the two cameras. Measurement of the additional camera angles advantageously improves quality control related to system image quality. In addition, the active material in the hot line features has been reduced to short sections near each end of each line for a significant reduction in manufacturing cost and handling radiation dose. Additionally, the phantom is designed to be free-standing, and to be stable on any surface, including a curved trough-like shape of the patient table. This allows the phantom to be placed at nearly any position along the centerline of the patient pallet. These and other exemplary advantages and features will be described in more details in the following description.

Although embodiments of the present framework are described in the context of an exemplary dual modality imaging system that includes a CT imaging system and a PET imaging system, it should be understood that other imaging systems capable of performing the functions described herein are contemplated as being used.

FIG. 1 is a block diagram illustrating an exemplary computer system 101 for implementing the framework as described herein. In some implementations, computer system 101 operates as a standalone device. In other implementations, computer system 101 may be connected via communication module 114 to other machines, such other computer systems 101. In a networked deployment, computer system 101 may operate as a peer machine in a peer-to-peer (or distributed) network environment. Any number of computer systems 101 may be provided (e.g., one, two, three or more) to serve one or more multi-modality imaging systems 120.

Computer system 101 may include a processor device or central processing unit (CPU) 104 coupled to one or more non-transitory computer-readable media 105 (e.g., computer storage or memory device), input-output devices 108 (e.g., monitor, mouse, touchpad or keyboard) and communication module 114 via an input-output interface 121. Computer system 101 may further include support circuits such as a cache, a power supply or battery, clock circuits and a communications bus (not shown). Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in one or more non-transitory computer-readable media 105. In particular, the present techniques may be implemented by an analysis module 107. Non-transitory computer-readable media 105 may include random access memory (RAM), read-only memory (ROM), magnetic floppy disk, flash memory, and other types of memories, or a combination thereof. The computer-readable program code is executed by processor device 104 to process data acquired by, for example, imaging system 120. The computer-readable program code is not intended to be limited to any particular programming language and implementation thereof. It will be appreciated that a variety of programming languages and coding thereof may be used to implement the teachings of the disclosure contained herein. The same or different computer-readable media 105 may be used for storing a database.

Multi-modality imaging system 120 acquires medical image data using at least two different modalities. For example, the first modality may be a Computed Tomography (CT) camera and the second modality may be Positron Emission Tomography (PET) camera. Other types of multi-modality imaging systems, such as a PET/ultrasound system or a CT/magnetic resonance imaging (MRI) system, may also be used.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
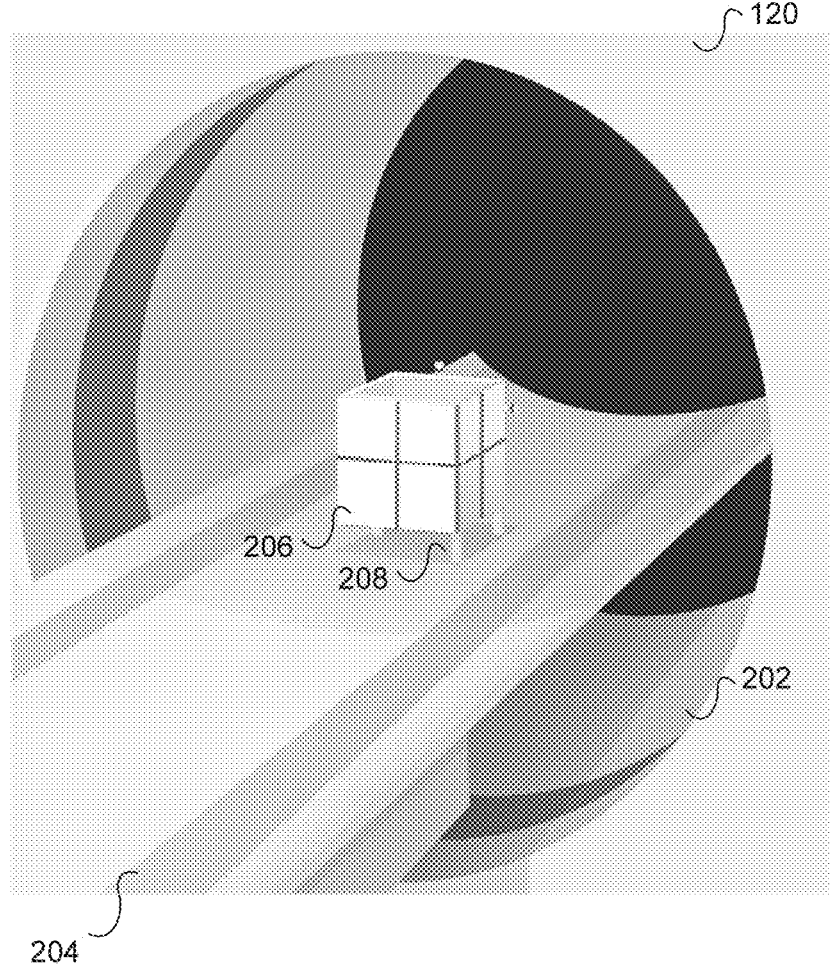
FIG. 2 shows a perspective view of an exemplary gantry of a multi-modality imaging system.

FIG. 2 shows a perspective view of an exemplary gantry 202 of a multi-modality imaging system 120. A patient handling system (PHS) may be used to move the patient table 204 axially into the gantry 202 through each camera of the multi-modality imaging system 120. Multi-modality imaging system 120 may include, for example, a CT camera with a tunnel for the patient and a PET camera with a tunnel for the patient. In some implementations, both cameras are rigidly mounted and are nominally orthogonal to the table travel vector, and nominally concentric about an axis parallel to the table travel.

An imaging phantom 206 may be positioned on the patient table 204. The phantom 206 may be designed to be free-standing. The width of the phantom 206 is substantially wide (e.g., around 150-500 mm) to be able to contain both hot and cold rods in space. Additionally, the phantom 206 is supported by three legs 208, so that it is stable on any surface, including the curved trough-like shape of the patient table 204.

Figure 3A:
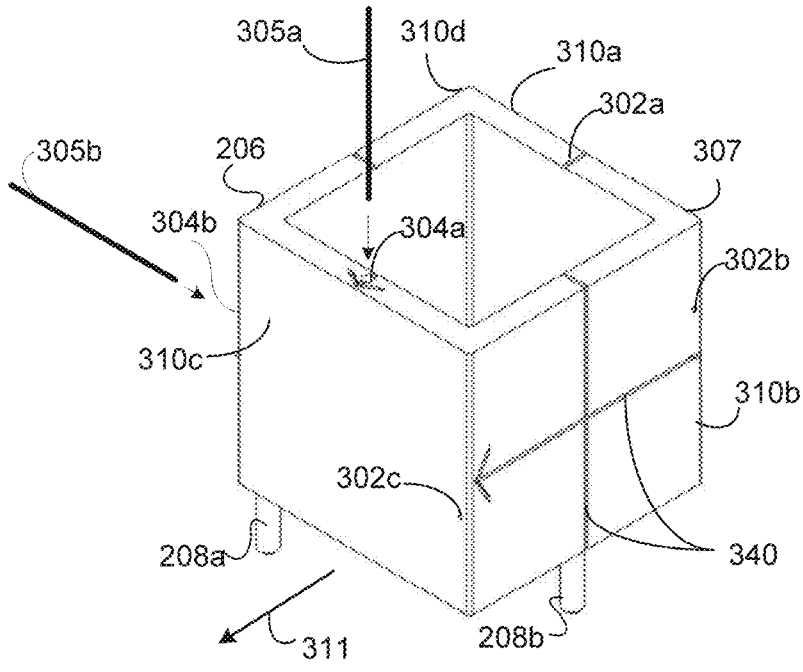
FIG. 3*a* shows a perspective view of an exemplary phantom.

FIG. 3a shows a perspective view of an exemplary phantom 206. In some implementations, phantom 206 has a housing 307 that is a box-like structure box supported by three legs. In this perspective view, only two legs (208a, 208b) are visible. Housing 307 includes first, second, third and fourth side plates (310a, 310b, 310c, 310d), wherein first and third plates (310a, 310c) are parallel to each other, and second and fourth plates (310b, 310d) are parallel to each other. First plate 310a is disposed at the rear of the phantom 206 (i.e., away from the gantry 202), while third plate 310c is disposed at the front of the phantom 206 (i.e., towards the gantry 202). It should be appreciated that other shapes, structures or configurations are also possible. The housing 307 is less dense than the hot and cold rods. The housing 307 may be less dense because it includes voids or air pockets in a shell-like structure that is three-dimensionally printed. In some implementations, the housing 307 is distinguishable from the hot and cold rods in CT images, and invisible in PET images acquired by the multi-modality imaging system 120. The housing 307 may include, for example, a plastic material (e.g., polyamide 12) that is three-dimensionally printed. Other non-radioactive housing materials with different machining operations are also useful.

In some implementations, the housing 307 includes one or more orientation markings 340 (e.g., line markings) engraved on the surfaces of the plates 310a-d to ensure adequate alignment. Before obtaining the measurements, imaging phantom 206 may be spatially oriented using system laser markers that are designed to align with the orientation markings 340. Advantageously, the phantom 206 may be placed at nearly any position along the centerline of the patient table 204, unlike previous phantoms there were designed to be supported only by a bracket at the tip of the patient table. This framework does not depend upon accurate orientation of the phantom 206 with respect to the cameras. Orientation within approximately 10 degrees from orthogonal with respect to the cameras and the table travel vector 311 is sufficient.

In some implementations, the phantom 206 encloses first and second hot rods 305a-305b that are visible in images acquired by both cameras (e.g., CT and PET) in multi-modality imaging system 120. First and second hot rods 305a-305b may be, for example, stainless steel tubes filled with a radioactive material (e.g., Ge-68, Na-22, F-18). Other materials, such as aluminum, may also be used to form the tubes. The radioactive material may be a solid or liquid solution. First and second hot rods 305a-305b may be removable to replace the radioactive material, and insertable into housing 307 and tightly held in place.

In some implementations, one or more segments in each hot rod 305a-305b are filled with the radioactive material. The segment may extend across substantially the entire length of the respective hot rod 305a-305b. Alternatively, the one or more segments include short segments located at both ends of the respective hot rod 305a-305b. The length of each short segment may be, example, less than one third of the total length of the respective hot rod 305a-b. For instance, the short segment may be 1 cm long and the total length of the hot rod may be 12 cm long. Advantageously, providing short segments enables a significant reduction in manufacturing cost and handling radiation dose.

First and second hot rods 305a-b are disposed in a plane that is substantially orthogonal to the travel vector 311. The maximum angle tolerance of the orthogonality between the hot rods 305a-b may be, for example, 0.5 degrees. First and second hot rods 305a-b may form a "T" configuration in the plane. Other configurations, such as an "X" configuration, are also useful. First and second hot rods 305a-b may be inserted through first hole 304a and second hole 304b in the third plate 310c at the front of phantom housing 307. First and second hot rods 305a-b are tightly inserted into the first hole 304a and second hole 304b such that they are stable and do not move, particularly during the multi-modality image acquisition process. In some implementations, the first hole 304a that receives first hot rod 305a is oriented nominally vertically, while the second hole 304b that receives second hot rod 305b is oriented nominally left-right horizontally. In some implementations, the hot rods 305a-b are placed in a plane at the front of the phantom 206 (i.e., toward gantry 202). When inserted into the first hole 304a and second hole 304b, first and second hot rods 305a-b are substantially orthogonal to each other, and can be used to measure the relative pitch and yaw angles between the two cameras. First and second hot rods 305a-b are used to provide the relative camera offsets in the translational and roll angle (about the travel axis) directions.

In some implementations, the phantom 206 further encloses first, second and third embedded cold rods. The cold rods may be, for example, stainless steel rods, ferrous material with high attenuation or other appropriate dense material that is visible only in images acquired by one modality (e.g., CT) but not in images acquired by the other different modality (e.g., PET) of the multi-modality imaging system 120. Unlike the hot rods (305a-b), the cold rods do not contain radioactive material and therefore do not have to be replaced. The cold rods may be permanently embedded in the phantom 206, which can be stored without shielding.

In some implementations, the cold rods are substantially orthogonal to each other. The maximum angle tolerance of orthogonality may be, for example, 0.15 degrees. In some implementations, the cold rods include first, second and third cold rods, wherein the first and second cold rods are substantially orthogonal to the table travel vector 311, and the third cold rod is substantially parallel to the travel vector 311. The cold rods may be fixedly embedded in third, fourth and fifth holes (302a, 302b, 302c) in the phantom housing 307 such that they are stable and do not move, particularly during the multi-modality image acquisition process. In some implementations, third hole 302a is disposed along a top edge of first plate 310a, fourth hole 302b is disposed on second plate 310b and fifth hole 302c is disposed on third plate 310c. First cold rod embedded in third hole 302a may be oriented nominally vertically, while second cold rod embedded in fourth hole 302b may be oriented nominally left-right horizontally and third cold rod embedded in fifth hole 302c may be oriented nominally axial horizontally. First and second cold rods are in a plane at the rear of the phantom 206 (i.e., away from gantry 202). The cold rods may be used to measure the pitch and yaw angles of one of the cameras (e.g., CT camera) with respect to the table travel vector 311.

Figure 3B:
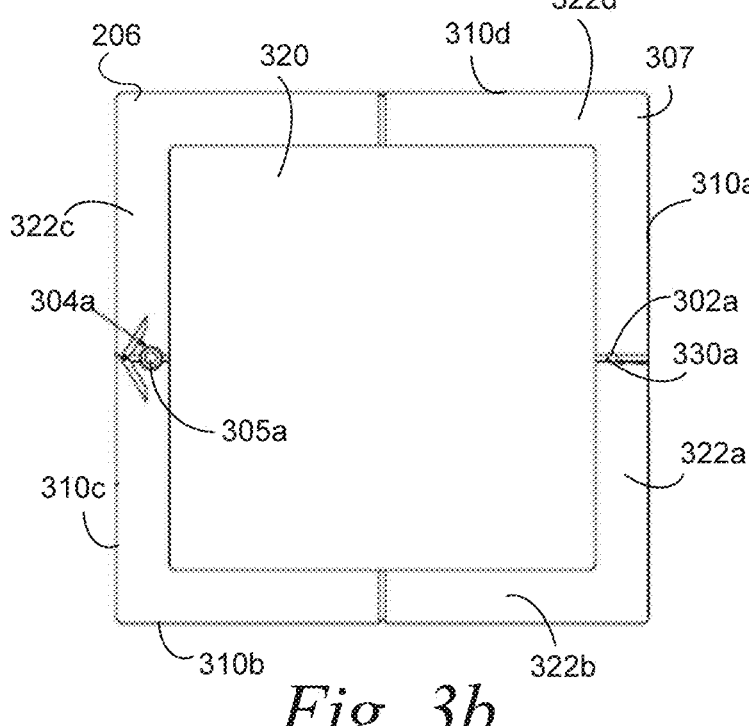
FIG. 3*b* shows a top view of an exemplary phantom.

FIG. 3b shows a top view of an exemplary phantom 206. The top view shows a square opening 320 formed by the upper edges 322a-d of first, second, third and fourth side plates (310a, 310b, 310c, 310d). In some implementations, there are two vertical rods (i.e., first removable hot rod 305a and first cold embedded rod 330a). A first hole 304a is disposed in the center of upper edge 322c of third side plate 310c to receive the first vertical hot rod 305a. A third hole 302a is disposed in the center of upper edge 322a of first side plate 310a to receive the first vertical cold rod 330a.

Figure 3C:
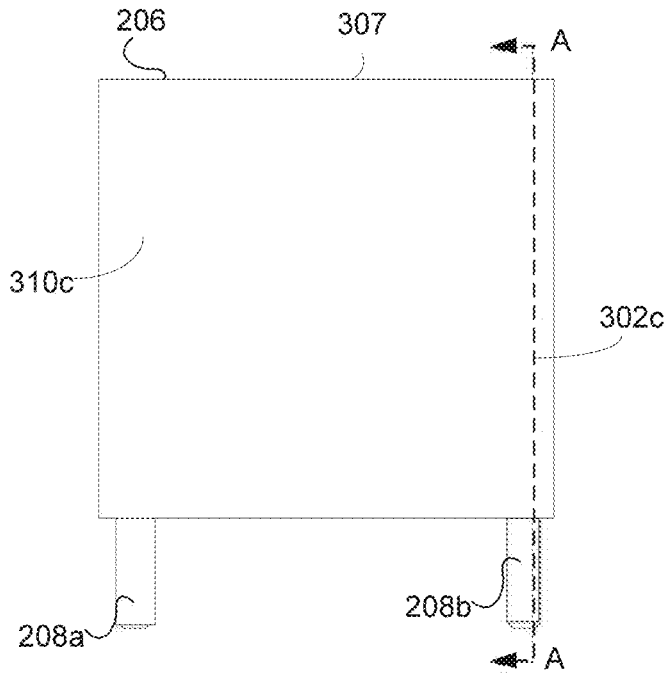
FIG. 3*c* shows a front view of third plate disposed at the front of the phantom.
Figure 3D:
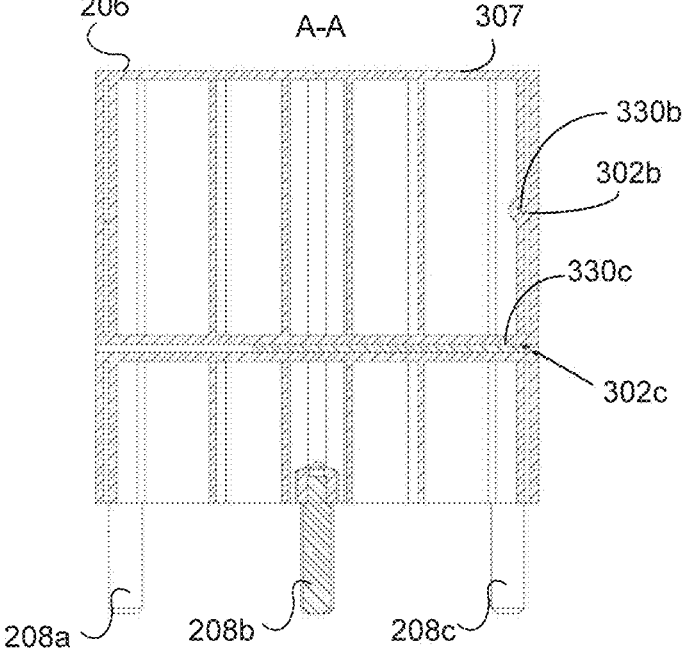
FIG. 3*d* shows a cross-sectional view along line A-A.

FIG. 3c shows a front view of third plate 310c disposed at the front of the phantom 206, while FIG. 3d shows a cross-sectional view along line A-A in FIG. 3c. As shown, phantom 206 has a housing 307 that forms a shell. The housing 307 is supported by three legs 208a-c. Second cold rod 330b may be inserted into fourth hole 302b in a left-right horizontal direction, while third cold rod 330c may be inserted into fifth hole 302c in an axial horizontal direction below second cold rod 330b.

Third cold rod 330c may be placed low (e.g., ⅓ the height of phantom 206) along the left side (when the hot rods are facing gantry 202). In some implementations, third cold rod 330c is shorter (e.g., 10 cm) than both first and second cold rods 330a-b (e.g., 15 cm). Third cold rod 330c may extend axially from the rear of the phantom 206 less than all the way (e.g., about ⅔ of the way) to the front of the phantom 206. This placement of the third cold axial horizontal rod 330c provides asymmetry, which advantageously facilitates robust recognition of the location and orientation of the phantom 206 in the image volume acquired by the first camera (e.g., CT camera), such that the placement of the phantom 206 by the user may be validated prior to the longer image acquisition by the second camera (e.g., PET camera) of the multi-modality imaging system 120.

Figures 3E, 3F:
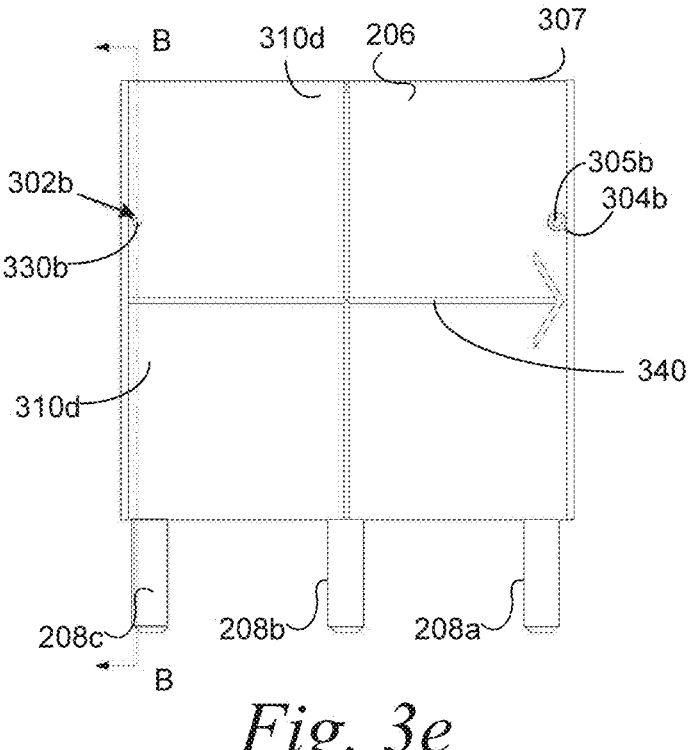
FIG. 3*e* shows a front view of fourth plate disposed at the right side of the phantom.
FIG. 3*f* shows a cross-sectional view along line B-B.

FIG. 3e shows a front view of fourth plate 310d disposed at the right side of the phantom 206. There are two left-to-right horizontal rods (second removable hot rod 305b and second cold embedded rod 330b) shown. Second cold rod 330b may be inserted into fourth hole 302b in a left-right horizontal direction, while second hot rod 305b may be inserted into second hole 304b in a left-right horizontal direction. Both second hole 304b and fourth hole 302b may be at the same height from the base of the housing 307.

FIG. 3f shows a cross-sectional view along line B-B in FIG. 3e. Second cold rod 330b may be inserted into fourth hole 302b in a left-right horizontal direction, while third cold rod 330c may be inserted into fifth hole 302c in an axial horizontal direction below second cold rod 330b. In some implementations, third cold rod 330c extends from the rear of the device (away from phantom 206) all the way to the front of the phantom 206. The ends of the second cold rod 330b may be capped with, for example, epoxy or other suitable material.

FIG. 4 shows an exemplary method 400 of image alignment. It should be understood that the steps of the method 400 may be performed in the order shown or a different order. Additional, different, or fewer steps may also be provided. Further, the method 400 may be implemented with computer system 101 of FIG. 1, multi-modality imaging system 120 of FIG. 2, phantom 206 of FIGS. 3a-f, a different system, phantom or device, or a combination thereof.

At 402, a first image of imaging phantom 206 is acquired using a first camera of first modality (e.g., CT) of multi-modality imaging system 120. The phantom 206 may include two removable hot rods 305a-b and three embedded cold rods 330a-c, as previously described. The phantom 206 is positioned on patient table 204. For instance, a user may place the phantom 206 on the patient table 204, then move the patient table 204 into the gantry 202 and turn on the laser alignment system of the multi-modality imaging system 120. The user may align the orientation markings 340 on the phantom 206 in all six degrees of freedom with the laser markings from the laser alignment system, adjusting the height of the patient table 204 as needed. A scan protocol may be loaded and initiated in multi-modality imaging system 120 to acquire the first image of the phantom 206. The first image is, for instance, a three-dimensional (3D) image volume. Analysis module 107 may reconstruct the first image using, for example, maximum intensity projection (MIP) or other suitable reconstruction algorithm. The reconstructed image may then be preprocessed to remove unwanted features, such as the patient table 204 and legs 208a-c.

Figure 5:
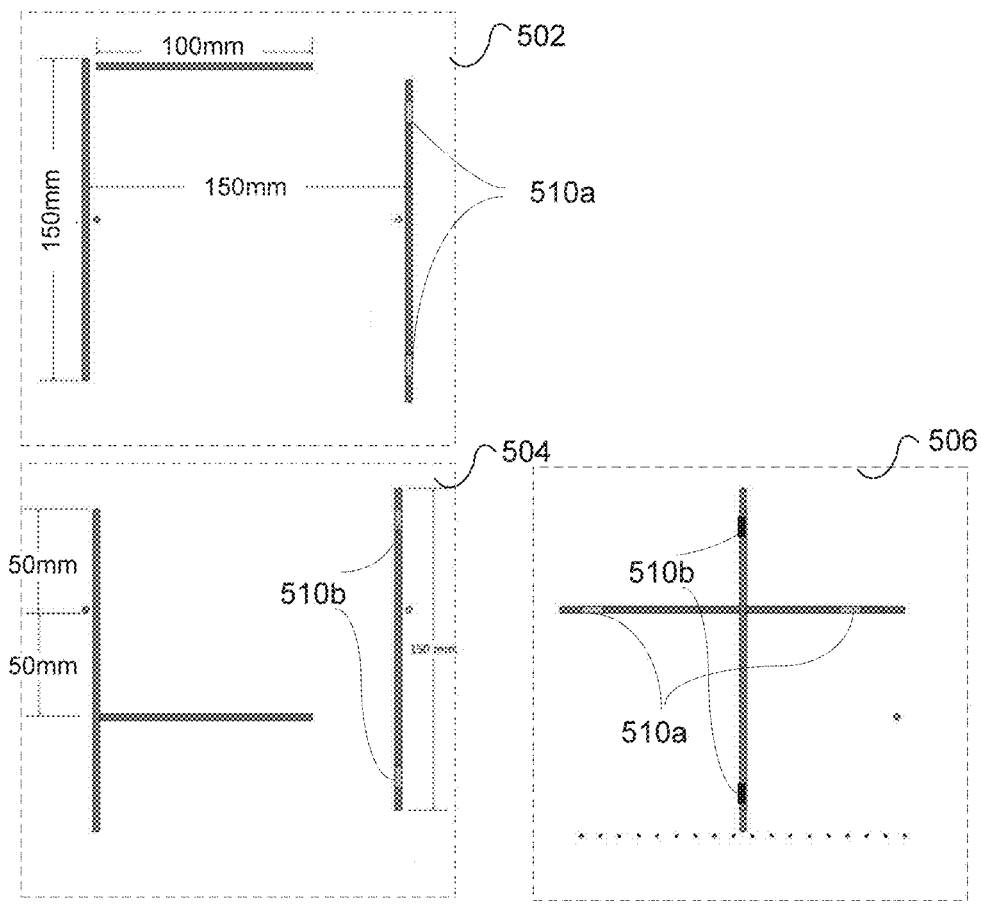
FIG. 5 shows exemplary slices of an exemplary reconstructed and preprocessed first image.

FIG. 5 shows exemplary slices 502-506 of an exemplary reconstructed and preprocessed first image. Slice 502 shows the plan view, slice 504 shows a side elevation view and slice 506 shows a front elevation view from the gantry 202. Segments 510a-b are the only segments that will visible in the second image.

Returning to FIG. 4, at 404, analysis module 107 determines tip centroids near top points and bottom points (or tips) of the two vertical rods in the first image. The two vertical rods may be a vertical hot rod 305a and a vertical cold rod 330a. It is not known at this point which rod is the hot rod 305a and which rod is the cold rod 330a.

Analysis module 107 may locate the top points of the two vertical rods by examining horizontal image slices from the top down. Even in the worst case of the phantom being placed 10 degrees away from the orthogonal line, there is a range of slices in which the tops of the two vertical rods 305a and 330a are the only features in the slice. Top points of the two vertical rods 305a and 330a are located at two spots with intensity above a pre-determined threshold value. At the worst-case angle, the tops of the two vertical rods 305a and 330a may be separated by a vertical distance of, for example, 38 mm. The bottom points of the vertical rods 305a and 330a may similarly be located by examining horizontal slices from the bottom up. For each vertical rod (305a, 330a), the 3D distance between the top and bottom points may be, for example, 150 mm±10 mm.

After the top and bottom points (or tips) are found, each rod may be traced slice-by-slice, moving vertically, as the peak location in each cross-sectional slice should be near (e.g., within a few millimeters of) the peak location in the adjacent slice. Following the peak locations, slice-by-slice, a range of slices located with a predetermined range of distance (e.g., between 10 mm to 20 mm) from the end of each tip may be identified for each vertical rod. For each of these ranges of slices, a Gaussian fit may be used to identify the centroid of each slice. The average of all the centroids of all of the slices may be determined in each of these 10 mm segments to create a single centroid near the top point and a single centroid near the bottom point of each rod.

At 406, analysis module 107 determines the next location of the phantom 206 for acquiring a second image using a second camera of second modality (e.g., PET) in the multi-modality imaging system 120. In some implementations, the next location of the phantom 206 may be determined based on the previously determined first tip centroids of the vertical rods. If the x position of the single cross-section of a rod in the first image is to the right of the average of the four x values for the first tip centroids (as viewed from the gantry 202), then the phantom 206 is placed with the "hot" rods 305a-b towards the gantry 202. In some implementations, the next position may be determined by calculating the average z location of the vertical rod closer to the gantry 202 plus half the field-of-view (FOV) length of the second camera minus the default Z offset. The tips of this rod that is closer to the gantry 202 is identified as the "hot" vertical rod 305a, and the tips of the other rod is identified as the "cold" vertical rod 330a.

Else, if the x position of the single cross-section of a rod is to the left of the average of the four x values for the centroids of the tips of the vertical rods (as viewed from the gantry 202), the phantom 206 is rotated 180° (in the horizontal plane), and the "hot" rods are away from the gantry 202. The next position for acquisition of the second image may be determined by calculating the average z location of the vertical rod further from the gantry plus half the FOV length of the second camera minus the default Z offset. The tips of this rod are identified as the "hot" vertical rod 305a, and the tips of the other rod is identified as the "cold" vertical rod 330a.

At 408, analysis module 107 determines second tip centroids of horizontal rods (305b and 330b-c) in the first image. In some implementations, to determine the second tip centroids, the shorter axial cold rod 330c are eliminated from the first image by deleting everything lower than a pre-determined distance (e.g., around 75 mm) below the top tip of the vertical cold rod 330a. The same way the vertical rods (305a, 330a) were found earlier, but working in sagittal slices inward from the left and the right, analysis module 107 may identify the left and right tips of the hot and cold horizontal rods (305b, 330b). Analysis module 107 may identify which horizontal rod is "hot" and which is "cold" by using the locations of the "hot" and "cold" vertical rods (305a, 330a). The distance between the tips of each rod may be, for example, 150 mm±10 mm. Analysis module 107 may determine a centroid for a segment from 10 mm to 20 mm from each tip, the same as was done for the vertical rods.

Returning to the original image containing the axial cold rod 330c, a cross-section of this rod may be located prior to acquiring the second image. From that location, analysis module 107 may work in coronal slices both forward and backward until the two tips of the axial cold rod 330c are found. The 3D distance between these two tips should be, for example, 100 mm±10 mm. Excluding the first slice at each tip meeting the threshold criteria, analysis module 107 may determine a centroid for a 10 mm segment near each tip, in the same manner as already done for the other four rods in the first image. The output may be six (x, y, z) points, two for each "cold" rod.

At 410, a second image of the phantom 206 at the determined location is acquired using a second camera of second modality (e.g., PET) of multi-modality imaging system 120. Prior to acquiring the second image, the phantom 206 may be moved to the determined location by using, for example, a patient-handling system (PHS) of the patient table 204. The second image may be a three-dimensional image volume. The second image may be acquired until sufficient image statistics are obtained.

At 412, analysis module 107 determines third tip centroids at or near the ends of each of the vertical and horizontal hot rods 304a-b. In some implementations, analysis module 107 examines the second image by horizontal slices from the top and from the bottom, and by sagittal slices from the left and from the right, until peak activity is found exceeding a pre-determined threshed value at each "tip". Once those tips are located, analysis module 107 may continue processing slices until the last slice is found exceeding the pre-determined activity threshold value for each rod.

For each of the four segments representing the hot rods 304a-b, analysis module 107 may exclude the first slice in which activity above threshold value was found, and calculate a centroid using the remaining slices (e.g., 8 mm of length) with activity. For each cross-section, in each slice, the center may be calculated using a Gaussian fit. For the vertical rod, this should produce several (x, z) pairs, with the y coordinate given by the slice location. For the horizontal rod, this should produce several (y, z) pairs, with the x coordinate given by the slice location. For each of the four segments, analysis module 107 may calculate the average of all of its (x, y, z) points to determine the location (x, y, z) of a single centroid.

For the vertical rod, the 3D distance between the top centroid and the bottom may be, for example, 130 mm±10 mm. For the horizontal rod, the 3D distance between the left centroid and the right centroid may be, for example, 130 mm±10 mm. While calculating the centroids for each segment, analysis module 107 may determine the sum of all the activity concentrations of all the pixels of each cross-section used, then divide the sum by the number of slices used. This provides an average activity for each hot rod. If the lesser of these is less than 70% of the greater, the workflow may be failed for mismatched sources. The output may be four (x, y, z) points representing the tip centroids, two for each hot rod 304a-b.

At 414, analysis module 107 determines misalignment parameters of the first and second cameras based on the first, second and third tip centroids. The misalignment parameters may be used for compensation in future acquisitions by the multi-modality imaging system 120 as well as quality control. The misalignment parameters may include, but are not limited to, absolute angular offsets (e.g., pitch, yaw) of the first and/or second camera with respect to the table travel vector 311, as well as relative translational offsets (e.g., X, Y, Z) and rotational offsets (e.g., pitch, yaw, roll) between the two cameras.

FIG. 6 shows a table 602 of exemplary misalignment parameters that may be determined for a CT-PET imaging system using the present framework. Relative translational offsets (X, Y, Z) and relative rotational offsets (pitch, yaw, roll) from the PET camera to the CT camera may be determined based on data from the two hot rods (305*a*, 305*b*). Absolute pitch and yaw values from the CT camera to the PHS (or gantry) may be determined based on data from the cold rods (330*a*, 330*b*, 330*c*). Absolute pitch and yaw values from the PET camera to the PHS (or gantry) may be determined based on data from both hot rods (305*a*. 305*b*) and cold rods (330*a*, 330*b*, 330*c*). For example, {absolute PET pitch, absolute PET yaw}={absolute CT pitch, absolute CT yaw}±{relative pitch offset, relative yaw offset}.

Figure 7A:
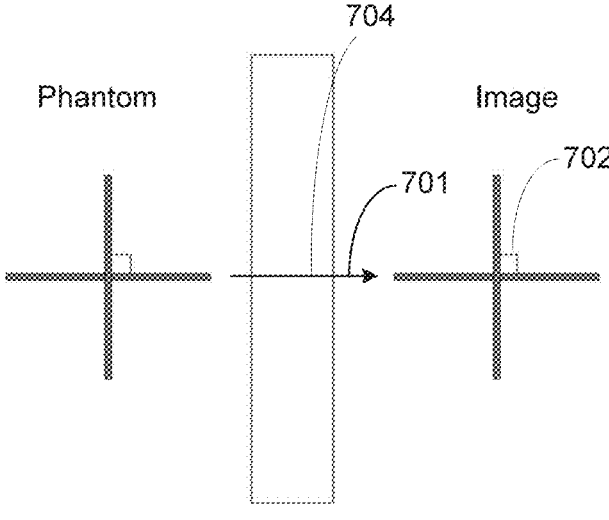
FIG. 7*a* illustrates a perfect alignment between the CT axis and the travel vector of the phantom in the gantry.
Figure 7B:
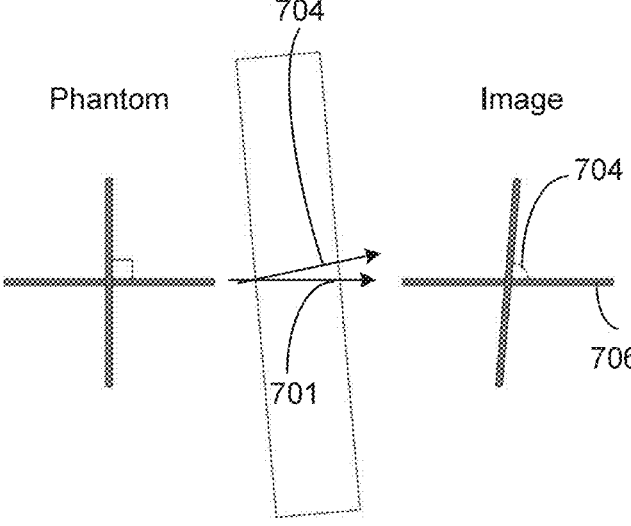
FIG. 7*b* illustrates an imperfect alignment between the CT axis and the travel vector of the phantom in the gantry.

A CT gantry angle may be determined. The CT gantry angle is the angle, in the pitch and/or yaw direction, of the CT gantry with respect to the table travel vector. Determination of the CT gantry angle is based on the skew of the image which occurs when the CT axis is not parallel to the travel vector of the table (or phantom) in the gantry. FIG. 7*a* illustrates a perfect alignment between the CT axis 704 and the travel vector 701 of the phantom in the gantry. In this illustration, the angle 702 between the two features (or rods) is 90° in the image acquired by the CT camera. FIG. 7*b* illustrates an imperfect alignment between the CT axis 704 and the travel vector 701 of the phantom in the gantry.

When the CT axis is not aligned with the travel vector 701, the angle 704 between the two features in the image acquired by the CT camera is changed by the same angle as the CT misalignment. It should be appreciated that the feature 706 parallel to the travel vector 701 is unaffected. It is not critical that the phantom itself be perfectly aligned with the travel vector (e.g., within 10° is fine). The features in the phantom need not intersect. The angle between the features of the phantom in the orthogonal projections should be known to serve as a reference for analysis of the acquired image. In an exemplary phantom, the angle between the features is 90°. Other known angles may also be used. This illustration applies equally for a side view (pitch angle) or a plan view (yaw angle).

In some implementations, the pitch angle of the CT camera with respect to the table travel vector 311 is determined by measuring the angle between the vertical and axial cold rods 330*a* and 330*c* in the first image. The difference from 90 degrees is the pitch angle of the CT camera with respect to the table travel vector 311.

Figure 8:
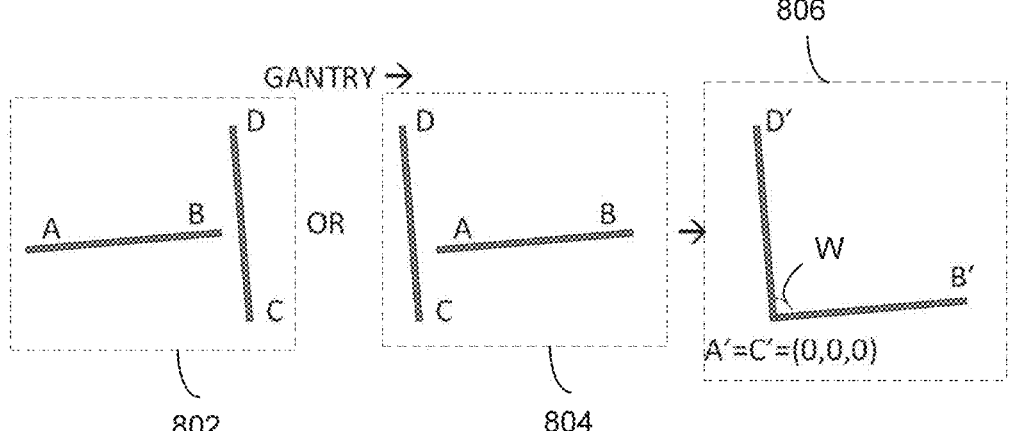
FIG. 8 shows an elevation view of exemplary vertical and axial cold rods.

FIG. 8 shows an elevation view of exemplary vertical and axial cold rods 330*a* and 330*c*. Point A represents the tip centroid of the axial cold rod 330*c* further from the gantry, while point B represents the tip centroid of the axial cold rod 330*c* nearer the gantry. Point C represents the tip centroid near the bottom of the vertical cold rod 330*a*, while point D represents the tip centroid near the top of the vertical cold rod 330*a*. There are two possible configurations (802, 804) of the lines AB and CD, wherein the vertical cold rod 330*a* represented by line CD is located near or away from the gantry.

To best visualize the angle between lines AB and CD, the lines may be translated (without changing their angles) so that they intersect at the origin (0, 0, 0), as shown in configuration 806. Line AB may be translated to line A'B', wherein A'=(0,0,0) and B'=B−A. Line CD may be translated to C'D', wherein C'=(0, 0, 0) and D'=D−C. The pitch angle of the CT camera with respect to the gantry may be determined by determining the difference of angle W from 90 degrees, where angle W is the angle between the two lines A'C' and C'D'. If the CT camera is leaning towards the PHS, angle W is less than 90 degrees. If the CT camera is leaning away the PHS, angle W is greater than 90°. The difference of angle W from 90° is the estimate of the CT-gantry pitch angle.

In some implementations, the yaw angle of the CT camera with respect to the travel vector is determined by measuring the angle between the left-right horizontal and axial cold rods (330*b*, 330*c*) in the first image acquired by the CT camera, and determining the difference of this angle from 90°.

Figure 9:
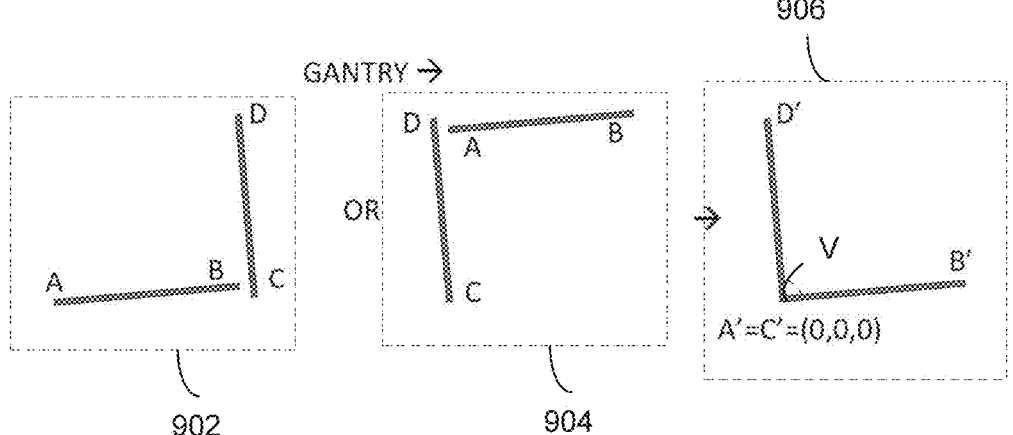
FIG. 9 shows a plan view of exemplary left-right horizontal and axial cold rods.

FIG. 9 shows a plan view of exemplary left-right horizontal and axial cold rods 330*b* and 330*c*. Point A represents the tip centroid of the axial cold rod 330*c* further from the gantry, while point B represents the tip centroid of the axial cold rod 330*c* nearer the gantry. Point C represents the tip centroid near the left end of the horizontal cold rod 330*b*, while point D represents the tip centroid near the right end of the horizontal cold rod 330*b*. There are two possible configurations (902, 904) of the lines AB and CD, wherein the horizontal cold rod 330*b* represented by line CD is located near or away from the gantry.

To best visualize the angle between lines AB and CD, the lines may be translated (without changing their angles) so that they intersect at the origin (0, 0, 0), as shown in configuration 906. Line AB may be translated to line A'B', wherein A'=(0,0,0) and B'=B−A. Line CD may be translated to C'D', wherein C'=(0, 0, 0) and D'=D−C. The yaw angle of the CT camera with respect to the travel vector may be determined by determining the difference of angle V from 90 degrees, wherein angle V is the angle between the two lines A'C' and C'D'. If the CT camera is rotated counterclockwise, angle V less than 90 degrees. If the CT camera is rotated clockwise, angle V is greater than 90°. The difference of angle V from 90° is the estimate of the CT-gantry yaw angle.

In some implementations, the relative translational and rotational offset parameters between the PET camera with respect to the CT camera may be determined based on the hot rods 305*a-b* that are visible in both the first and second images. It may not be sufficient to simply calculate a six-dimensional transform that matches the PET lines in the second image to the corresponding CT lines in the first image. Such process assumes rotations about the centroid of the features, rather than the center of the image, and results in erroneous x, y, and z offsets, which increases the further the phantom is from the 3D isocenter of the PET detectors in the PET camera.

Therefore, in some implementations, the rotational (i.e., pitch, yaw, roll) offsets are calculated first, and the PET image is rotated by all three angles with the 3D isocenter of the PET detectors as the center of rotation, and the translational offsets (i.e., X, Y, Z offsets) are calculated using this corrected PET image. Alternatively, the translational offsets are calculated by a method which eliminates the sensitivity to the pitch, yaw and roll angles. Such computation may be performed by, for example, a "one step" matrix.

Alternatively, the rotational offsets may be determined using the tip centroids of hot rods 305*a-b* as follows: 1) pitch offset may be determined by projecting the vertical hot rod 305*a* in the first and second images (e.g., PET and CT) to a sagittal plane, and finding the angle between the two lines in the sagittal plane; 2) yaw offset may be determined by projecting the horizontal hot rod 305*b* in the first and second images to a horizontal plane, and finding the angle between the two lines in the horizontal plane; and 3) roll offset may be determined by projecting the vertical hot rod 305*a* in the first and second images to a coronal plane, and finding the angle between the two lines in the coronal plane.

Consider a horizontal x axis and a vertical y axis which applies to each coronal slice of an image, each with its origin at the isocenter axis. By considering only the intercepts of the detected lines with these axes, the effect of the angles is minimized. For example: For a 0.5° rotation, a feature 200 mm from the axis is moved by 1.7 mm (proportional to tan (0.5°)), but (assuming that feature defines a near-vertical line), its intercept with the x axis is only moved by 0.008 mm (proportional to 1−cos (0.5°)).

In some implementations, relative translational offsets of the PET camera with respect to the CT camera are determined using the tip centroids of hot rods 305a-b as follows: 1) X offset may be determined by calculating the x values at which the vertical hot rod 305a intercepts the x-axis in the first and second images, and determining the difference between these x values; 2) Y offset may be determined by calculating the y values at which the horizontal hot rod 305b intercepts the y-axis in first and second images, and determining the difference between these y values; and 3) Z offset may be determined by first calculating the z value at which the vertical hot rod 305a intercepts the x-axis in the second image as a distance from the back of the second image, calculating the slice location at which the vertical hot rod 305a intercepts the x-axis in first image, and calculating the Z offset as follows: CT slice location (a negative number)− PHS position during PET acquisition (a more negative number)+Distance of intercept to back of PET (a positive number). The convention for calculating the distance to the back of PET should match the convention which is used for assigning slice locations to PET slices in corrected PET images. Z offset calculation may be repeated using the horizontal "hot" rod 305b and the z values at which it intercepts the y-axes in the first and second images. The two resulting Z offset values may be checked against each other, and so that the average of the two values may be used to optimize the accuracy of the final Z offset value.

In some implementations, the pitch angle of the PET camera with respect to the table travel vector 311 is determined from the pitch angle of the CT camera with respect to the table travel vector 311 and the pitch offset. Whether the pitch offset is added or subtracted depends upon the sign convention of the pitch offset. The sign convention for the PET gantry pitch angle should match that of the CT gantry pitch angle.

In some implementations, the yaw angle of the PET camera with respect to the table travel vector 311 is determined from the yaw angle of the CT camera with respect to the table travel vector 311 and the yaw offset. Whether the yaw offset is added or subtracted depends upon the sign convention of the yaw offset. The sign convention for the PET gantry yaw angle should match that of the CT gantry yaw angle.

In some implementations, analysis module 107 checks the values of the calculated misalignment parameters to determine if they are less than a pre-determined threshold values. If the misalignment parameters are acceptable, they may be stored and used for image compensation in future image acquisitions by the multi-modality imaging system 120. The misalignment parameters may be applied to align images acquired by the multi-modality imaging system 120.

The following is a list of non-limiting illustrative embodiments disclosed herein:

Illustrative embodiment 1. An imaging phantom for alignment of medical images acquired by a multi-modality imaging system, comprising: a housing; first, second and third cold rods enclosed by the housing, wherein the first, second and third cold rods are substantially orthogonal to each other, wherein the first and second cold rods are orthogonal to a travel vector, and the third cold rod is substantially parallel to the travel vector, wherein the first, second and third cold rods are visible only in images acquired by a first camera of the multi-modality imaging system; and first and second hot rods enclosed by the housing, wherein the first and second hot rods are visible in images acquired by both the first camera and a second camera of the multi-modality imaging system, wherein the first and second cameras comprise different modalities.

Illustrative embodiment 2. The imaging phantom of illustrative embodiment 1 wherein the first camera comprises a computed tomography (CT) camera and the second camera comprises a positron emission tomography (PET) camera.

Illustrative embodiment 3. The imaging phantom of any one of illustrative embodiments 1-2 wherein the first and second hot rods are disposed in a plane that is substantially orthogonal to the travel vector.

Illustrative embodiment 4. The imaging phantom of any one of illustrative embodiments 1-3 wherein the first and second hot rods are substantially orthogonal to each other.

Illustrative embodiment 5. The imaging phantom of any one of illustrative embodiments 1-4 wherein the first and second hot rods comprise a radioactive material disposed in one or more segments of each of the first and second hot rods.

Illustrative embodiment 6. The imaging phantom of illustrative embodiment 5 wherein the one or more segments comprise a segment that extends across substantially an entire length of each of the first and second hot rods.

Illustrative embodiment 7. The imaging phantom of illustrative embodiment 5 wherein the one or more segments comprise short segments located at both ends of each of the first and second hot rods.

Illustrative embodiment 8. The imaging phantom of any one of illustrative embodiments 1-7 wherein the first, second and third cold rods are used to measure pitch and yaw angles of the first camera with respect to the travel vector.

Illustrative embodiment 9. The imaging phantom of any one of illustrative embodiments 1-8 wherein the third cold rod is shorter than the first and second cold rods.

Illustrative embodiment 10. The imaging phantom of any one of illustrative embodiments 1-9 wherein the housing comprises a shell-like structure that is three-dimensionally printed.

Illustrative embodiment 11. The imaging phantom of any one of illustrative embodiments 1-10 wherein the housing is supported by three legs.

Illustrative embodiment 12. A method of image alignment, comprising: acquiring a first image of a phantom positioned on a patient table using a first camera of first modality in a multi-modality imaging system, wherein the phantom includes first and second hot rods and first, second and third cold rods enclosed by a housing, wherein the first and second hot rods are disposed in a plane that is substantially orthogonal to a travel vector of the patient table, wherein the first and second cold rods are substantially orthogonal to the travel vector, and the third cold rod is substantially parallel to the travel vector; acquiring a second image of the phantom using a second camera of second modality in the multi-modality imaging system; and determining misalignment parameters of the first and second cameras based on the first and second images.

Illustrative embodiment 13. The method of illustrative embodiment 12 wherein the first and second hot rods comprise a vertical hot rod and a left-right horizontal hot rod.

Illustrative embodiment 14. The method of any one of illustrative embodiments 12-13 wherein the first, second and third cold rods comprise a vertical cold rod, a left-right horizontal cold rod and an axial horizontal cold rod.

Illustrative embodiment 15. The method of illustrative embodiment 14 further comprising: determining first tip centroids of the vertical hot rod and the vertical cold rod in the first image; and determining second tip centroids of the left-right horizontal hot rod, the left-right horizontal cold rod and an axial cold rod in the first image.

Illustrative embodiment 16. The method of illustrative embodiment 15 further comprising: determining, based on the first tip centroids, a next location of the phantom for acquiring the second image of the phantom; and moving the phantom to the next location prior to acquiring the second image of the phantom.

Illustrative embodiment 17. The method of illustrative embodiment 15 further comprising determining third tip centroids of the vertical hot rod and the left-right horizontal hot rod in the second image.

Illustrative embodiment 18. The method of illustrative embodiment 17 further comprising determining the misalignment parameters based on the first, second and third tip centroids.

Illustrative embodiment 19. The method of any one of illustrative embodiments claim 12-18 wherein determining the misalignment parameters comprises determining angular offsets of the first camera with respect to the travel vector, angular offsets of the second camera with respect to the travel vector, and relative translational and rotational offsets between the first and second cameras.

Illustrative embodiment 20. One or more non-transitory computer-readable media embodying instructions executable by machine to perform operations, comprising: acquiring a first image of a phantom positioned on a patient table using a first camera of first modality in a multi-modality imaging system, wherein the phantom includes two hot rods and three cold rods of known geometry; acquiring a second image of the phantom using a second camera of second modality in the multi-modality imaging system; and determining misalignment parameters of the first and second cameras based on the first and second images.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. An imaging phantom for alignment of medical images acquired by a multi-modality imaging system, comprising:
    a housing;
    first, second and third cold rods enclosed by the housing, wherein the first, second and third cold rods are orthogonal to each other, wherein the first and second cold rods are orthogonal to a travel vector, and the third cold rod is parallel to the travel vector, wherein the first, second and third cold rods are visible only in images acquired by a first camera of the multi-modality imaging system; and
    first and second hot rods enclosed by the housing, wherein the first and second hot rods are visible in images acquired by both the first camera and a second camera of the multi-modality imaging system, wherein the first and second cameras comprise different modalities.

2. The imaging phantom of claim 1 wherein the first camera comprises a computed tomography (CT) camera and the second camera comprises a positron emission tomography (PET) camera.

3. The imaging phantom of claim 1 wherein the first and second hot rods are disposed in a plane that is orthogonal to the travel vector.

4. The imaging phantom of claim 1 wherein the first and second hot rods are orthogonal to each other.

5. The imaging phantom of claim 1 wherein the first and second hot rods comprise a radioactive material disposed in one or more segments of each of the first and second hot rods.

6. The imaging phantom of claim 5 wherein the one or more segments comprise a segment that extends across an entire length of each of the first and second hot rods.

7. The imaging phantom of claim 5 wherein the one or more segments comprise short segments located at both ends of each of the first and second hot rods.

8. The imaging phantom of claim 1 wherein the first, second and third cold rods are used to measure pitch and yaw angles of the first camera with respect to the travel vector.

9. The imaging phantom of claim 1 wherein the third cold rod is shorter than the first and second cold rods.

10. The imaging phantom of claim 1 wherein the housing comprises a shell-like structure that is three-dimensionally printed.

11. The imaging phantom of claim 1 wherein the housing is supported by three legs.

12. A method of image alignment, comprising:
    acquiring a first image of a phantom positioned on a patient table using a first camera of first modality in a multi-modality imaging system, wherein the phantom includes first and second hot rods and first, second and third cold rods enclosed by a housing, wherein the first and second hot rods are disposed in a plane that is orthogonal to a travel vector of the patient table, wherein the first and second cold rods are orthogonal to the travel vector, and the third cold rod is parallel to the travel vector;
    acquiring a second image of the phantom using a second camera of second modality in the multi-modality imaging system; and
    determining misalignment parameters of the first and second cameras based on the first and second images.

13. The method of claim 12 wherein the first and second hot rods comprise a vertical hot rod and a left-right horizontal hot rod.

14. The method of claim 12 wherein the first, second and third cold rods comprise a vertical cold rod, a left-right horizontal cold rod and an axial horizontal cold rod.

15. The method of claim 14 further comprising:
    determining first tip centroids of the vertical hot rod and the vertical cold rod in the first image; and
    determining second tip centroids of the left-right horizontal hot rod, the left-right horizontal cold rod and an axial cold rod in the first image.

16. The method of claim 15 further comprising:
    determining, based on the first tip centroids, a next location of the phantom for acquiring the second image of the phantom; and
    moving the phantom to the next location prior to acquiring the second image of the phantom.

17. The method of claim 15 further comprising determining third tip centroids of the vertical hot rod and the left-right horizontal hot rod in the second image.

18. The method of claim 17 further comprising determining the misalignment parameters based on the first, second and third tip centroids.

19. The method of claim 12 wherein determining the misalignment parameters comprises determining angular offsets of the first camera with respect to the travel vector, angular offsets of the second camera with respect to the travel vector, and relative translational and rotational offsets between the first and second cameras.

20. One or more non-transitory computer-readable media embodying instructions executable by machine to perform operations, comprising:

acquiring a first image of a phantom positioned on a patient table using a first camera of first modality in a multi-modality imaging system, wherein the phantom includes two hot rods and three cold rods of known geometry;

acquiring a second image of the phantom using a second camera of second modality in the multi-modality imaging system; and determining misalignment parameters of the first and second cameras based on the first and second images.

* * * * *